United States Patent [19]
Cammilli et al.

[11] Patent Number: 5,545,204
[45] Date of Patent: Aug. 13, 1996

[54] SEQUENTIAL CARDIOSTIMULATION SYSTEM (DDD) USING A SINGLE ELECTROCATHETER INSERTED THROUGH THE CORONARY SINUS

[76] Inventors: Leonardo Cammilli, Via Caselli, 11, 50100 Firenze; Gino Grassi, Via F. Pasqui, 31, 50019 Sesto Fiorentino (Firenze), both of Italy

[21] Appl. No.: 207,571

[22] Filed: Mar. 7, 1994

[30] Foreign Application Priority Data

Mar. 8, 1993 [IT] Italy .................. FI93A0041

[51] Int. Cl.⁶ ................................... A61N 1/05
[52] U.S. Cl. ........................... 607/123; 128/642
[58] Field of Search .................... 607/123, 122, 607/119, 116; 128/642

[56] References Cited

U.S. PATENT DOCUMENTS

| | | | |
|---|---|---|---|
| 3,825,015 | 7/1974 | Berkovits | 607/123 |
| 4,135,518 | 1/1979 | Dutcher | 128/642 |
| 4,498,482 | 2/1985 | Williams | 607/122 |
| 4,567,901 | 2/1986 | Harris | 607/123 |
| 4,928,688 | 5/1990 | Mower | 607/9 |
| 5,127,403 | 7/1992 | Brownlee | 607/122 |
| 5,165,403 | 11/1992 | Mehra . | |
| 5,304,139 | 4/1994 | Adams et al. | 607/122 |
| 5,350,404 | 9/1994 | Adams et al. | 607/122 |

*Primary Examiner*—William E. Kamm
*Assistant Examiner*—Kennedy J. Schaetzle
*Attorney, Agent, or Firm*—McGlew and Tuttle, P.C.

[57] ABSTRACT

Electrocatheter for sequential cardiostimulation, comprising one or more atrial electrodes and one or more ventricular electrodes connectable to a dual chamber pacemaker via respective interface connectors, said electrocatheter being suitably shaped to allow the insertion thereof into the coronary sinus so as to position the atrial electrodes within the coronary sinus in correspondence of the left atrium of the heart, and the ventricular electrodes within the great cardiac vein where the anterior interventricular begins, in correspondence of the left ventricle, wherein the ventricular electrodes are located close to the distal end of the catheter to allow the ventricular stimulation and sensing, and wherein the atrial electrodes are suitably spaced from the ventricular ones and disposed upstream thereof to permit the atrial stimulation and sensing. (FIG. 1)

20 Claims, 3 Drawing Sheets

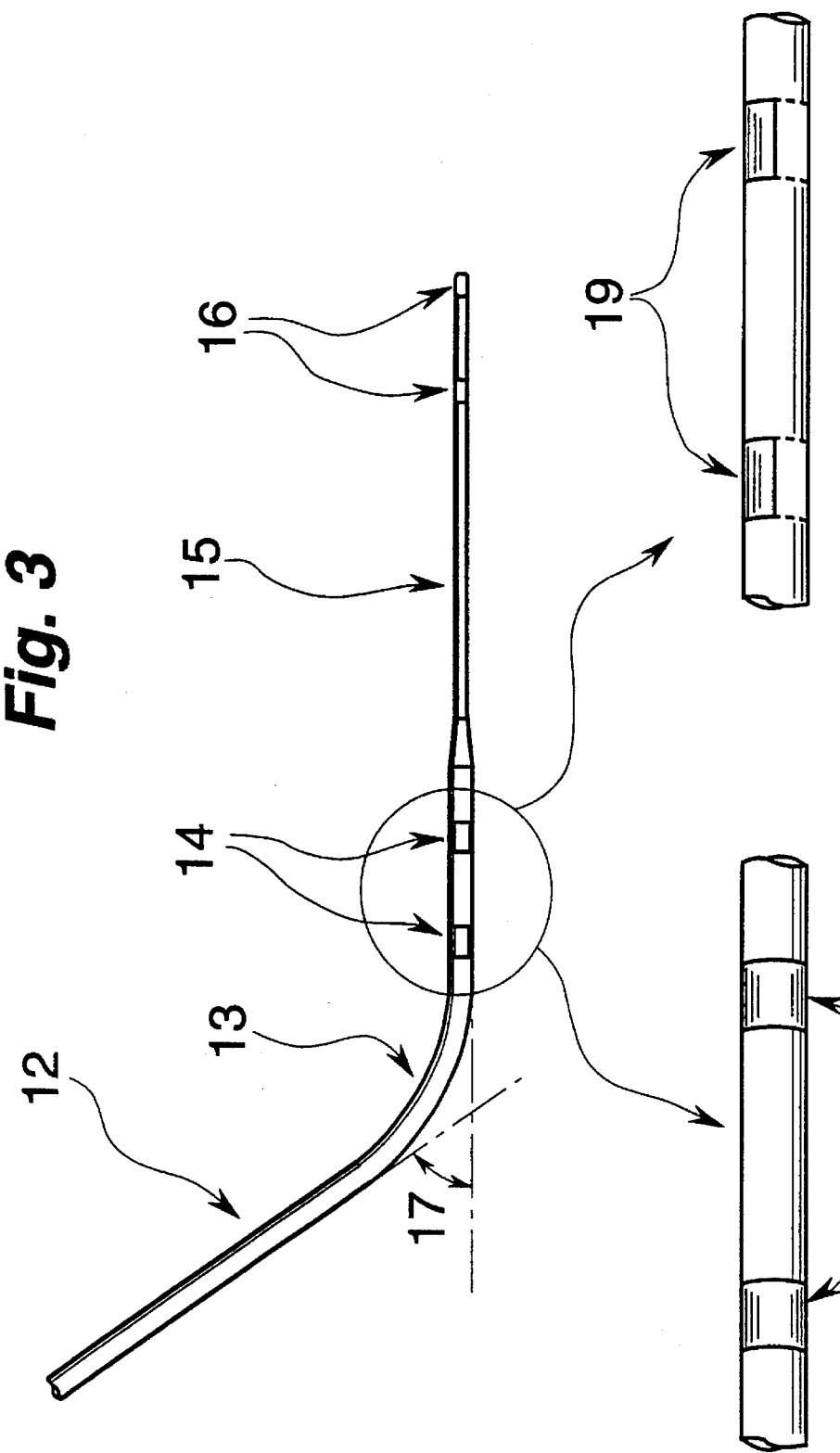

SEQUENTIAL CARDIOSTIMULATION SYSTEM (DDD) USING A SINGLE ELECTROCATHETER INSERTED THROUGH THE CORONARY SINUS

FIELD OF THE INVENTION

The object of this patent is a DDD or DDR sequential in dual chamber cardiostimulation system using a single catheter carrying both the atrial and ventricular electrodes and being positioned through the coronary sinus, as illustrated in FIG. 1.

SUMMARY AND OBJECTS OF THE INVENTION

The preformation of the catheter and its electrodes arrangement, to be described later on, are such that the insertion of the electrocatheter into the coronary sinus allows the insertion of the ventricular electrode(s) into the great cardiac vein so as to establish a contact with the left ventricle. The atrial electrodes are predisposed at such a distance [from the free end of the catheter] as to result positioned in the middle part of the coronary sinus and in contact with the left atrium.

Experiments carried out on animals have shown that the system allows acceptable signal stimulation and sensing thresholds which match those obtainable from separate catheters inside the right auricle and ventricle.

The proposed system provides-for the use of normal DDD or DDDR pacemakers with no adaptation, allows a correct positioning of the electrocatheter, and a proper cardiac stimulation.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 3 is a view of the electrocatheter showing the angular relationship between first and second portions of the first section;

FIG. 4 is a view of the active surface of the atrial electrodes encompassing the whole circumference of a length of the catheter; and FIG. 5 is a view of the atrial electrodes showing the active surface covering only a portion of the circumference of the catheter.

Figure 1:
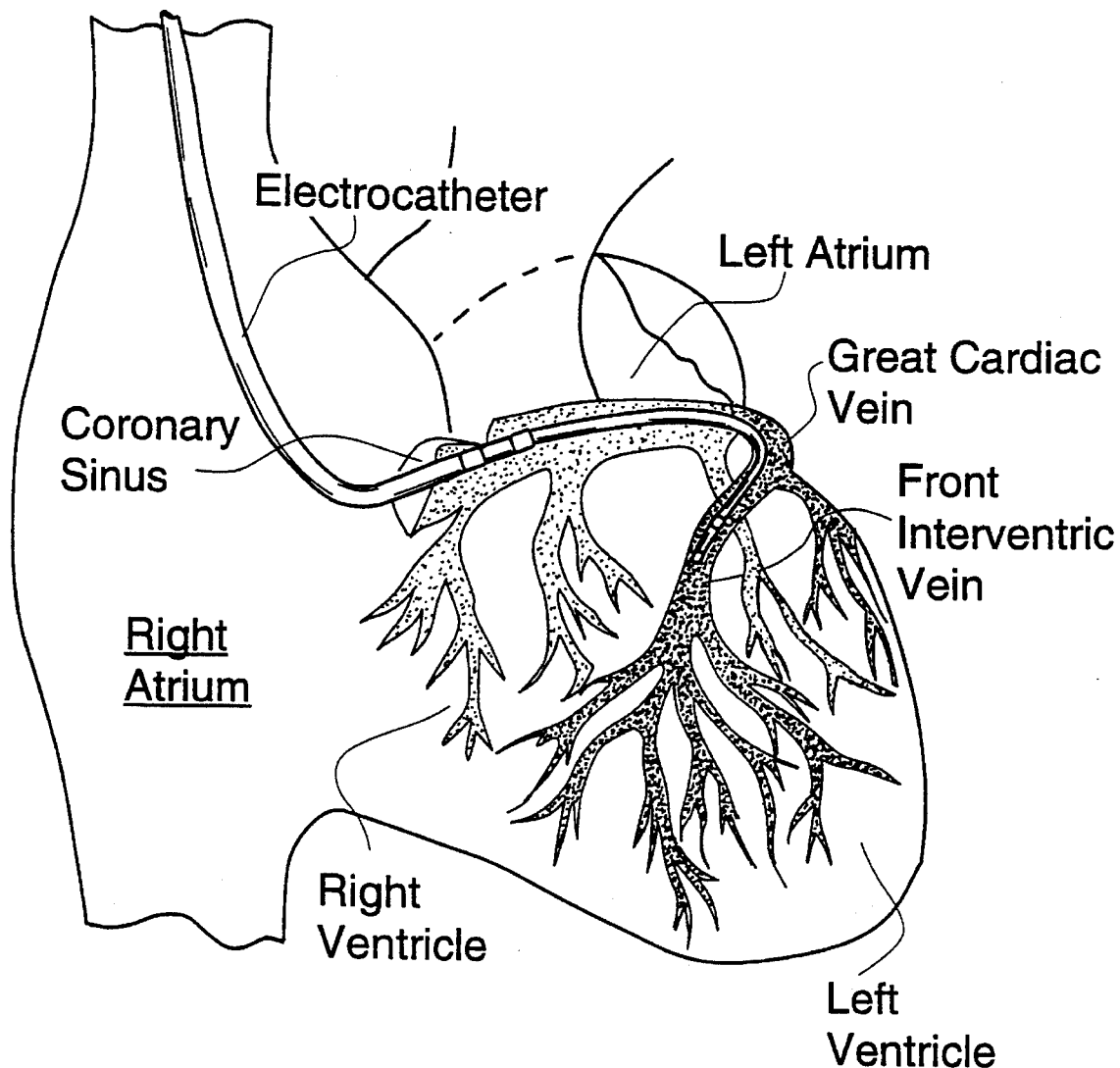
FIG. 1 is a view of an electrocatheter inside a heart.

DETAILED DESCRIPTION OF THE PREFERRED EMBODIMENT a) The segment 15 carrying the ventricular electrode(s) 16 shall have a diameter not higher than 5 Fr. (1.7 mm) or 6 Fr. (2 mm), and be very flexible so as to allow for its introduction into the great cardiac vein by following the curve thereof around the atrioventricular sulcus and not obstructing the same vein with its bulk.

To this end, provision is made, advantageously, for the use of a single ventricular electrode (thus achieving a monopolar stimulation), so as to maintain the bore of the distal part 15 of the catheter in the neighbourhood of 4 Fr. (1.35 mm). The ventricular electrode (or the electrodes) shall however remain implanted in the first half portion of the great cardiac vein, beyond the curve which leads it to the tip of the left ventricle, where the internal diameter is again of about 3–4 mm.

The electrocatheter, likewise those in use for usual positioning, shall be constructed in such a way as to allow for the introduction of a mandrel therewithin. The mandrel being able to stiffen the same electrocatheter upon the implantation thereof in the vein. This may be accomplished by the known technique using, as a conductor, a multiwire spiral having a lumen allowing the passage of the mandrel therethrough.

b) The catheter may change its dimensions at a point whose distance from the distal catheter can be preset between 50 and 80 mm so as to contain also the conductors of the atrial electrodes 14. The section 12 of the catheter may reach a diameter of 8–9 Fr (2.7–3 mm). This section, in fact, is intended to remain in the coronary sinus whose inner diametral is sufficiently large (8–15 mm).

The first (distal) of the two atrial electrodes 14 will be positioned at a distance of 50 to 80 mm from the tip of the catheter, while the second (proximal) electrode will be positioned at a distance of 5 to 20 mm therefrom.

Owing to the different dimensions that the heart may exhibit according to the age, sex and other factors, the electrocatheters designed according to the object of this patent, shall have to be produced in several sizes to be used in different conditions.

The atrial electrodes (see FIGS. 4 and 5) may be conformed either as shown at 19, that is, only radially uncovered on the side facing the atrium, and isolated on the opposite side, or as shown at 18, that is, in the form of two fully conductive rings.

The preferable, but not binding solution, is the one shown at 19, which makes it possible to limit the propagation of the electrical field arising from the stimulus in the direction of the ventricle and, at the same time, to facilitate the recording of the signals coming from the atrium, with respect from the ventricular signals.

According to a further embodiment of the invention, provision is made for the use of one single electrode 14 instead of two electrodes.

c) The section 12 of the electrocatheter exhibits a preformed curve 13 located at a distance of 15 to 25 mm from the atrial proximal electrode, so that the angle 17 of FIG. 3 will be in the range of 50° to 90°, with a preferable, not binding, value of about 60°.

This preformation has two purposes: the first is to facilitate the insertion of the eletrocatheter into the coronary sinus; the second is to have the atrial electrodes 19 always facing the inside of the curve and thus the atrium. These electrodes shall be actually fixed on the catheter in that position, so that the uncovered conductive part will remain turned towards the atrium.

The electrocatheter shall have a useful length like that of the usual endocavitary catheters for permanent stimulation: for example (not binding) a length in the range of 58 to 62 cm.

Figure 2:
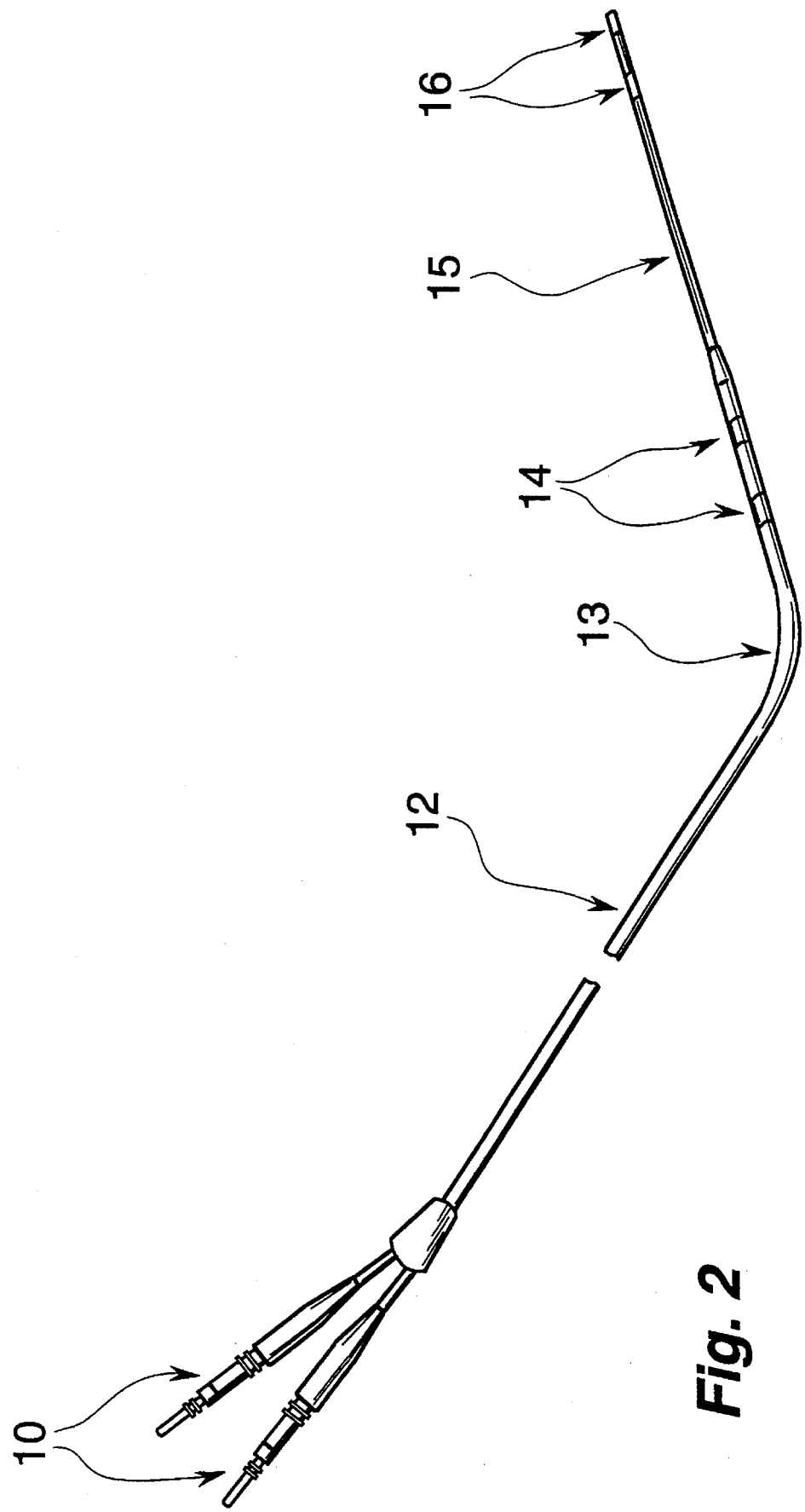
FIG. 2 is a perspective view of the electrocatheter.

Predisposed in the proximal part of the catheter are connecting plugs compatible with the selected pacemaker. The not-binding example of FIG. 2 refers to the most widely spread solution, that is, the one in which two IS-1-type bipolar or monopolar plugs are provided according to the solution adopted for the atrial and ventricular electrodes.

However, all the combinations and configurations as required for the used pacemaker may also be implemented.

The arrangement of the conductors in the catheter may be carried out, as a not binding examples, through one of the following solutions. One of these utilizes multilumen tubes of flexible and biocompatible materials (silicone, polyurethane or the like): inside each lumen a conductor will be inserted, preferably consisting of spiral-wound wires to achieve the maximum mechanical resistance. The spiral, which will be made to arrive at the distal ventricular electrode, shall be such to allow the insertion of a catheter-stiffening and guiding mandrel during the introduction into the vein and the positioning in the heart of the catheter, as well known in the clinic practice of implantation of cardiac stimulators.

A further possible solution is the use of coaxial spirals, isolated to each other and to the outside by thin-walled tubes made in flexible, insulating and biocompatible materials (polyurethane, teflon, silicone or similar).

The conductors material shall have high mechanical resistance and be biocompatible, such as the MP35N or ELGILOY, or similar.

The catheter may be inserted into the cephalic, jugular or subclavian vein, such as for the usual endocardiac catheters.

As it results from experimental researches, the proposed system exhibits excellent electrophysiologic characteristics. The stimulation thresholds reach values comparable with, or just slightly greater than those obtainable when positioning separate electrocatheters in the right auricle and ventricle. Also the detected electrical cardiac signals are comparable with the usual ones.

The measured stimulation thresholds are in the range of 0.5 to 1.5 Volt for the ventricular ones and of 0.8 to 1.6 for the atrial ones.

The detected signals are 5–10 mV for the ventricle and 1.2 and 2.8 mV for the atrium.

While specific embodiments of the invention have been shown and described in detail to illustrate the application of the principles of the invention, it will be understood that the invention may be embodied otherwise without departing from such principles.

We claim:

1. Electrocatheter for sequential cardiostimulation, comprising one or more atrial electrodes and one or more ventricular electrodes connectable to a dual-chamber pacemaker, said electrocatheter being suitably shaped to allow the insertion thereof into the coronary sinus so as to position the atrial electrode within the coronary sinus in correspondence of the left atrium of the heart, and the ventricular electrode within the great cardiac vein where the anterior interventricular begins, in correspondence of the left ventricle, wherein said ventricular electrode is located in proximity of the distal end of the catheter to allow for ventricular stimulation and sensing, and wherein the atrial electrode is suitably spaced from the ventricular electrode and shaped for atrial stimulation and sensing.

2. Electrocatheter according to claim 1, wherein a number of said atrial is two: and a distance between said two atrial electrodes being comprised between 5 and 20 mm.

3. Electrocatheter according to claim 1, comprising:— a first section with two straight portions whose axes form an angle between 50° and 80° and are joined by a curvilinear portion, the first straight portion being connectable to the dual-chamber pacemaker, and the second portion being provided with the atrial electrodes;—a second section of diameter lower than that of the first one, that is, of less than 2 mm, at the free end of which the ventricular electrodes are disposed, and which develops on the extension of the longitudinal axis of said portion containing the atrial electrodes.

4. Electrocatheter according to claim 1, wherein an active surface of said atrial electrodes is made to face a concavity of the catheter.

5. Electrocatheter according to claim 1, wherein the active surface of said atrial electrode is ring-like developed along the whole circumference of a corresponding length of the catheter.

6. Electrocatheter according to claim 1, comprising a plurality of conductors in the form of a multiwire spiral intended to power said atrial and ventricular electrodes, said spiral forming means for receiving a guide mandrel to cause stiffening and guiding of the electrocatheter during implantation.

7. Electrocatheter according to claim 6, further comprising:

a tubular form made of a flexible and biocompatible material from the group of silicone and polyurethane, said multiwire spiral is inserted inside said tubular form.

8. Electrocatheter according to claim 1, made up of a plurality of coaxial metal spirals which are isolated to each other and to the external environment by corresponding tubular thin-walled elements made of flexible, insulating and biocompatible material.

9. A sequential cardiostimulation electrocatheter comprising:

an atrial electrode for atrial stimulation and sensing;

a body, said body having a shape for insertion into a coronary sinus to position said atrial electrode within the coronary sinus in correspondence of a left atrium of a heart;

a connector positioned on one end of said body, said connector being connectable to a dual-chamber pacemaker;

a ventricular electrode positioned on said body at a position adjacent a distal end of said body substantially opposite said connector, said ventricular electrode being positioned on said body, having a shape, and being electrically connectable to the dual-chamber pacemaker through said connector, for ventricular stimulation and sensing, said body being shaped to position said ventricular electrode within a great cardiac vein where said anterior interventricular vein begins;

an atrial electrode positioned on said body at a position spaced from said ventricular electrode, said atrial electrode being positioned on said body, having a shape, and being electrically connectable to the dual-chamber pacemaker through said connector for atrial stimulation and sensing.

10. An electrocatheter in accordance with claim 9, wherein:

said atrial electrode is positioned substantially 50 to 80 mm from said distal end of said body.

11. An electrocatheter in accordance with claim 9, further comprising:

another atrial electrode positioned on said body, and shaped for atrial stimulation and sensing, said another atrial electrode being positioned from said atrial electrode by a distance in a range of 5 to 20 mm.

12. An electrocatheter in accordance with claim 9, further comprising:

another ventricular electrode positioned on said body and shaped for ventricular stimulation and sensing, said another ventricular electrode being positioned from said ventricular electrode by a distance in a range of 5 to 20 mm.

13. An electrocatheter in accordance with claim 9, wherein:

said body includes a first section with first and second substantially straight portions, said first and second portions being angularly spaced by an angle in a range of 50 to 80 degrees, said first and second portions being joined by a curvilinear portion, said first portion being connected to said connector and said second portion including said atrial electrode, said body also including a second section with a diameter less than a diameter of said first section, said second section being positioned at an end of said first section substantially opposite said connector, said second section including said ventricular electrode.

14. An electrocatheter in accordance with claim 9, wherein:

said body is curved to form a concavity;

an active surface of said atrial electrode only faces said concavity of said body.

15. An electrocatheter in accordance with claim 9, wherein:

an active surface of said atrial electrode is positioned along a whole circumference of a length of said body.

16. An electrocatheter in accordance with claim 9, further comprising:

a plurality of conductors in said body for electrically connecting said ventricular and said atrial electrodes to said connector, said plurality of conductors being formed into a spiral to define means for receiving a mandrel for stiffening and guiding of said body.

17. An electrocatheter in accordance with claim 16, wherein:

said body is formed in a tubular form and of flexible biocompatible material, said spiral being positioned inside said tubular form.

18. An electrocatheter in accordance with claim 9, wherein:

said body includes a plurality of coaxial metal spirals isolated from each other, said body also includes a tubular element made of flexible, insulating and biocompatible material, said tubular element isolating said coaxial metal spirals from an external environment.

19. A sequential cardiostimulation electrocatheter comprising:

a body, said body includes a first section with first and second substantially straight portions, said first and second portions being angularly spaced by an angle in a range of 50 to 80 degrees, said first and second portions being joined by a curvilinear portion, said body also including a second section with a diameter less than a diameter of said first section, said second section being positioned at an end of said first section substantially opposite said connector;

a connector positioned on one end of said body and connected to said first portion, said connector being connectable to a dual-chamber pacemaker;

a ventricular electrode positioned on said second section of said body at a position adjacent a distal end of said body substantially opposite said connector, said ventricular electrode being positioned on said body, having a shape, and being electrically connectable to the dual-chamber pacemaker through said connector, for ventricular stimulation and sensing;

an atrial electrode positioned on said second portion of said body at a position spaced from said ventricular electrode, said atrial electrode being positioned on said body, having a shape, and being electrically connectable to the dual-chamber pacemaker through said connector for atrial stimulation and sensing.

20. A sequential cardiostimulation electrocatheter comprising:

a body, said body being curved to form a concavity;

a connector positioned on one end of said body, said connector being connectable to a dual-chamber pacemaker;

a ventricular electrode positioned on said body at a position adjacent a distal end of said body substantially opposite said connector, said ventricular electrode being positioned on said body, having a shape, and being electrically connectable to the dual-chamber pacemaker through said connector, for ventricular stimulation and sensing;

an atrial electrode positioned on said body at a position spaced from said ventricular electrode, said atrial electrode being positioned on said body, having a shape, and being electrically connectable to the dual-chamber pacemaker through said connector for atrial stimulation and sensing, an active surface of said atrial electrode only facing said concavity of said body.

* * * * *